United States Patent [19]

Iwahara et al.

[11] Patent Number: 4,996,341
[45] Date of Patent: Feb. 26, 1991

[54] CONDENSED BICYCLIC DISILANYLENE-ACETYLENE COMPOUND AND METHOD FOR PREPARING THE SAME

[75] Inventors: Takahisa Iwahara, Kobe, Japan; Robert C. West, Madison, Wis.

[73] Assignee: Kanegafuchi Chemical Industry Co., Ltd., Japan

[21] Appl. No.: 548,231

[22] Filed: Jul. 5, 1990

[51] Int. Cl.$^5$ .................................................. C07F 7/08
[52] U.S. Cl. .................................................. 556/406
[58] Field of Search .......................................... 556/406

[56] References Cited

U.S. PATENT DOCUMENTS

| | | | |
|---|---|---|---|
| 4,845,255 | 7/1989 | Iwahara et al. | 552/406 |
| 4,866,153 | 9/1989 | Bortolin et al. | 556/406 X |

FOREIGN PATENT DOCUMENTS

| | | | |
|---|---|---|---|
| 0152891 | 9/1983 | Japan | 556/406 |
| 0152892 | 9/1983 | Japan | 556/406 |
| 0152893 | 9/1983 | Japan | 556/406 |

*Primary Examiner*—Paul F. Shaver
*Attorney, Agent, or Firm*—Welsh & Katz

[57] ABSTRACT

A condensed bicyclic disilanylene-acetylene compound having the following formula:

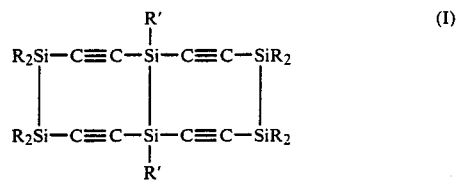

wherein R and R' are independently a univalent hydrocarbon group having 1 to 20 carbon atoms. The compound has a high degree of $\sigma$-$\pi$ electron delocalization.

21 Claims, No Drawings

CONDENSED BICYCLIC DISILANYLENE-ACETYLENE COMPOUND AND METHOD FOR PREPARING THE SAME

BACKGROUND OF THE INVENTION

The present invention relates to a cyclic ring compound and a method for preparing the same and more particularly, to a condensed bicyclic disilanylene-acetylene compound and a method for preparing the same.

Various types of organic, metal organic, and inorganic materials are known to have unusually high anisotropic properties and potentially useful electric, optical, and/or magnetic properties. Such materials are known to be useful in fabricating electrically conducting materials, semi-conductors, electronic devices, and electromagnetic or acoustic sensors. The utility of some of these materials may frequently be limited by such factors as weight, mechanical fragility, fabrication problems, corrosion, scarcity, and high costs.

Electroconductive organic materials have properties which can overcome or minimize such problems, and have the capability to be easily fabricated into films, filaments, and other shapes. Some of these materials are simply an organic material containing a conductive material therein, such as a metal or graphite. Others comprise organic materials whose electrical conductivities are established by chemical doping with electron acceptor and/or electron donor dopants. In general, the materials susceptible of establishing such electrical conductivity are characterized by highly delocalized $\pi$ electron conjugation, as may be found in most cyclic compounds, or sometimes by $\sigma$-electron delocalization which may be found in polysilanes as well as the Si-C heterocyclic compounds.

Electron delocalization between Si-Si $\sigma$ bonds and $\pi$ systems has been established for conjugated polysilyl compounds containing unsaturated or aromatic groups. Such $\sigma$-$\pi$ electron delocalization results in a strong ultraviolet absorption around 220 to 270 nm. Especially strong ultraviolet absorption at 250 nm has been found in the strained cyclic disilanylene-acetylene compound shown in formula (I):

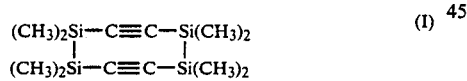

The compound of formula (IV) was obtained from the application of either heat or light to the nine-membered ring compound shown below.

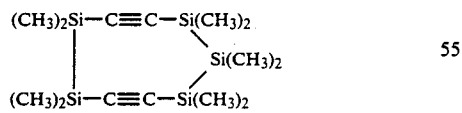

The compound of formula (I), because of its strong absorption in the near 250 nm wavelength, should have a high degree of $\sigma$-$\pi$ electron delocalization and therefore a high potential for use as an electroconductive material as well as an optical material. In addition, possibilities exist that the ring of the cyclic molecule might be opened and the cleaved molecule polymerized through the use of an anionic, cationic or radical reagent, including Na, K, methoxide, ethoxide, t-butoxide, lithium amide, sodium amide, acetylide, butyllithium, $BF_3$, $BCl_3$, $AlCl_3$, $TiCl_4$, triethylaluminium, azobisisobutyronitrile and benzoyl peroxide. Further, like polysilanes or polycarbosilanes, the compound of formula (I) should undergo conversion to silicon carbide when heated to high temperatures.

It is an object of the present invention to provide a new class of cyclic silane compound with $\sigma$-$\pi$ electron conjugation, specifically, a condensed bicyclic silane compound, and a method for preparing the same.

A further object of the present invention is to provide a novel condensed bicyclic disilanylene-acetylene compound and a method for preparing the same.

These and other objects of the present invention will become apparent from the description hereinafter.

SUMMARY OF THE INVENTION

The present invention provides a condensed bicyclic disilanylene-acetylene compound having the following formula (II):

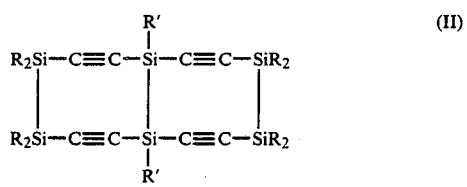

wherein R and R' are independently a univalent hydrocarbon group having 1 to 20 carbon atoms.

The present invention further provides a method for preparing the condensed bicyclic disilanylene-acetylene compound of formula (II), comprising the steps of:

(a) forming a diGrignard reagent by reacting a 1,2-diethynyldisilane having the following formula (III):

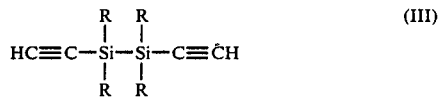

wherein R is the same as defined above, with a Grignard reagent;

(b) reacting the resulting diGrignard reagent with a 1,1,2,2-tetrachlorodisilane having the following formula (IV):

wherein R' is the same as defined above; and (c) isolating the resulting condensed bicyclic disilanyleneacetylene compound of formula (II).

DETAILED DESCRIPTION

The desired compound of the present invention is condensed bicyclic disilanylene-acetylene compounds represented by formula (II).

The groups R and R' in formula (II) are preferably alkyl groups having 1 to 20 carbon atoms, especially 1 to 8 carbon atoms, and aryl groups having 6 to 20 carbon atoms, especially 6 to 12 carbon atoms. Examples of the alkyl group are $CH_3$, $C_2H_5$, $n-C_3H_7$, $i-C_3H_7$, $n-C_4H_9$, $i-C_4H_9$, $t-C_4H_9$, $n-C_5H_{11}$, $n-C_6H_{13}$, n—$C_7H_{15}$ and n—$C_8H_{17}$. Examples of the aryl group are phenyl, and substituted phenyl groups such as tolyl and xylyl. The preferred group R is $CH_3$, $C_2H_5$, n—$C_3H_7$, i—$C_3H_7$, n—$C_4H_9$ and phenyl, especially $CH_3$. The preferred group R' is i—$C_3H_7$ and phenyl. The preferred compounds of formula (II) are that wherein R is —$CH_3$ and R' is i—$C_3H_7$ and that wherein R is —$CH_3$ and R' is phenyl.

The compound of formula (II) may have a cisconfiguration or a trans-configuration with respect to the two groups R' bonded to the different silicon atoms. The compound (II) of the present invention includes the cis-isomer, the trans-isomer and a mixture of the cis-isomer and the trans-isomer.

The desired compound (II) of the present invention is prepared by the following method.

The synthesis of the bicyclic disilanylene-acetylene compound (II) begins with the preparation of a diGrignard reagent. A 1,2-diethynyldisilane of formula (III) is reacted with a Grignard reagent, i.e., an alkylmagnesium halide or arylmagnesium halide, such as ethylmagnesium bromide, in an inert solvent such as tetrahydrofuran (THF). Other Grignard reagents such as methylmagnesium bromide, methylmagnesium iodide, n-propylmagnesium chloride, n-butylmagnesium chloride, secbutylmagnesium chloride, t-butylmagnesium chloride and phenylmagnesium chloride may also be used.

The resulting diGrignard reagent is preferably then reacted with a 1,1,2,2-tetrachlorodisilane of formula (IV) in an inert solvent such as THF. The reaction is carried at a temperature ranging from a room temperature to the reflux temperature for an hour to a week to yield a bicyclic disilanylene-acetylene compound of formula (II). Usually the reaction is conducted by refluxing the reaction mixture or by allowing the reaction mixture to stand at a room temperature. Such procedures may be repeated alternately.

In general, THF is preferably used as a reaction solvent in each of the reactions in the method of the present invention. However, other ethereal solvents, such as diethyl ether, di-n-butyl ether, dimethoxyethane, dioxanes, etc. may also be used, as known in the art.

In the case of the reaction of the diGrignard reagent with the compound (IV), it is important that the concentration of the reagents in the reaction solution be lower to avoid the I3 possibility of a chain extending polymerization reaction dominating. The concentration of each reagent is preferably about 0.5 M or lower. Polymerization is observed even in dilute solutions, but if both a dilute solution of the diGrignard reagent and a dilute solution of the tetrachlorodisilane are simultaneously added to THF in a reaction vessel, the cyclization reaction should dominate.

The amount of the Grignard reagent is preferably from 1.5 to 3.0 moles per 1 mole of the 1,2-diethynyldisilane. The amount of the diGrignard reagent is preferably from 1.5 to 3.0 moles per 1 mole of the tetrachlorodisilane.

The desired compound (II) is isolated from the reaction mixture preferably by a solvent extraction as follows: The reaction mixture is evaporated to remove the solvent. The residue is extracted with an organic solvent. Examples of the organic solvent are hexane, pentane, cyclohexane, ether, benzene, toluene, xylenes, chloroform, methylene chloride, etc. The preferred solvents are hexane, pentane, ether, benzene, toluene and chloroform. The organic layer is washed, dried and evaporated to give a crude product. The crude product is purified in a usual manner such as recrystallization or column chromatography, yielding a pure product of formula (II).

The desired compound of the present invention, for example, the compound (V) prepared in Example 1, has an absorption maximum at 260 nm in a ultraviolet-visible light spectral region, which shows that the compound has a higher degree of $\sigma$-$\pi$ electron delocalization than the cyclic compound of formula (I). Therefore, the condensed bicyclic compound of the present invention should have a high potential for use as an electroconductive material as well as an optical material, like the compound (I).

The compound (II) of the present invention has a possibility that its ring might be opened and the cleaved molecule polymerized through the use of an anionic, cationic or radical reagent, like the compound (I). Further, like polysilanes or polycarbosilanes, the compound (II) should undergo conversion to silicon carbide when heated to high temperatures.

In preparing the above compounds (II) for the exhibition of electroconductive properties, the process commonly referred to as doping can be utilized. A wide variety of doping materials may suitably be employed to attain electrical conductivity of the compound. Doping materials suitable for effecting an increase in the electrical conductivity of the condensed bicyclic disilanylene-acetylene compound (II) are generally electron acceptor dopants, including for example $I_2$, $Br_2$, ICl, IBr, $SbF_5$, $AsF_5$, $Cl_2$, HBr, $BF_3$, $BCl_3$, $SO_2$, $SO_3$, $Cl_2$, $NO_2$, HCN, ICN, $O_2$, $SiF_4$, NO, $C_2H_2$, and transition metal carbonates, phosphine, and olefin derivatives.

In doping, the compound (II) prepared by the method of the present invention is contacted by a dopant which may take place in a gaseous or vapor phase, or in a solution. In any case, doping is effected by uptake of the dopant molecules into the bicyclic disilanylene acetylene compound (II) which occurs pursuant to a degree proportional to the dopant concentration and the contacting period. For example, the bicyclic disilanylene-acetylene compound (II), in solid form, may be contacted by the gas $AsF_5$ under a reduced pressure, for example, 10 Torr, or may be placed in a melt of $SbF_5$, for a contacting period ranging from a few minutes to over 24 hours to provide the desired degree of doping as known in the art. The doped substance may thereby be provided with a room temperature electroconductivity within the range of from about $10^{-1}$ to $10^{-10}$ ohm$^{-1}$cm$^{-1}$ as measured using conventional techniques.

The doping procedure may also be carried out by placing the bicyclic disilanylene-acetylene compound (II) in a solution of a dopant in an appropriate organic solvent inert to the bicyclic disilanylene-acetylene compound (II), such as for example THF, n-hexane, or toluene. By trial and error, the length of time necessary to leave the bicyclic disilanylene-acetylene compound (II) in the solution is determined which will obtain the desired degree of doping. At the completion of the doping, the doped material is removed from the solution and rinsed in an additional amount of the organic solvent to remove any residual doping solution therefrom. The excess solvent is pumped off by a vacuum and the conductivity of the disilanylene-acetylene compound is measured as known in the art.

Further, some of the bicyclic disilanylene-acetylene compounds (II) of the present invention, for example, the compound (V) prepared in the below-mentioned Example 1, are heated to 1,100° C. or higher under an argon atmosphere and are thereby transformed to SiC.

The 1,1,2,2-tetrachlorodisilane (IV) used as a starting material in the present invention can be prepared by the following methods:

(1) R'=alkyl group

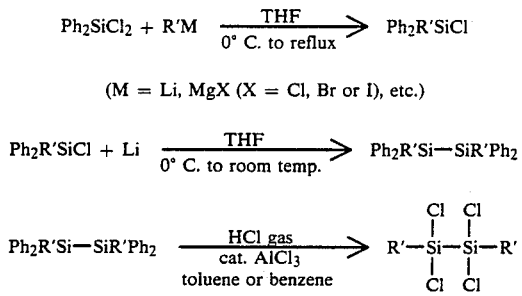

(M = Li, MgX (X = Cl, Br or I), etc.)

The compound (IV) wherein R' is methyl group, 1,2-dimethyl-1,1,2,2-tetrochlorodisilane, is a known compound prepared by the method of the following publication (cf. H. Sakurai, T. Watanabe and M. Kumada, J. Organomet. Chem., 7, 15(1967).

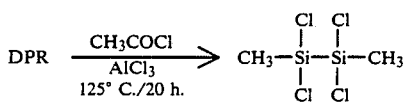

DPR means the fraction boiling over the range about 150° to 160° C. from the distillation residue of the direct synthesis of methylchlorosilanes.

(2) R'=aryl group

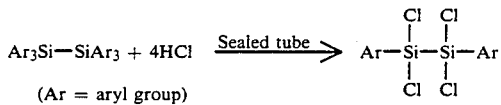

(Ar = aryl group)

The compound (IV) wherein R' is phenyl group, 1,2-diphenyl-1,1,2,2-tetrachlorodislane, is a known compound (cf. E. Hengge, G. Bauer, E. Brandstatter and G. Kollmann, Monatsh. Chem., 106, 887(1975)).

The present invention is more specifically described and explained by means of the following Examples. In the Examples, the reactions were conducted under a nitrogen gas atmosphere, unless otherwise noted.

PREPARATION OF PRECURSOR COMPOUNDS

Synthesis of diphenylisopropylchlorosilane

Into 200 ml of dry THF was dissolved 160 g (0.63 mole) of diphenyldichlorosilane. To this was added dropwise 450 ml (0.90 mole) of a 2.0 M solution of isopropylmagnesium chloride in THF at a room temperature over 20 minutes. A mildly ethothermic reaction was observed. After the conclusion of the dropwise addition, the reaction mixture was refluxed for 3 days. The formed salt and the solvent were removed from the reaction mixture. The residue was distilled under a reduced pressure to give 130 g of a colorless clear liquid (b.p. 116° to 118° C./0.22 Torr).

The product was determined to contain 94% by weight of diphenylisopropylchlorosilane by a gas chromatographic analysis The yield calculated on the basis of the purity was 74%.

$^1$H NMR (200 MHz, CDCl$_3$)
1.12 (d, 6 H, SiCH(CH$_3$)$_2$),
1.69 (septet, 1 H, SiCH(CH$_3$)$_2$),
7.30-7.50 (m, 6 H, phenyl),
7.54-7.72 (m, 4 H, phenyl)

Synthesis of 1,2-diisopropyl-1,1,2,2-tetraphenyldisilane

A 1 liter three necked flask was charged with 200 ml of dry THF and then 5.04 g (0.73 mole) of small pieces of lithium metal was quickly added. To this was added dropwise 155 g of diphenylisopropylchlorosilane (purity: 94% by weight, 0.56 mole) at a room temperature over 2 hours. A mildly exothermic reaction was observed. After the dropwise addition, the reaction mixture was agitated for 3 days. The reaction mixture turned red purple. The formed salt and the solvent were removed from tho reaction mixture. To the residue was added about 300 ml of benzene, whereby the residue was dissolved therein. The benzene solution was washed with a saturated aqueous solution of ammonium chloride (300 ml×3 times) and then with water (300 ml×1 time) and dried over anhydrous magnesium sulfate. The drying agent was filtered off and the filtrate was concentrated to give 128 g of a crude product in a pale yellow solid.

The crude product was recrystallized from a mixed solvent of hexane/THF (10/1 by volume) to give 48.5 g of a product having a purity of 100%. The second recrystallization gave 30.0 g of a product having a purity of 74%. The total yield was 57%.

Synthesis of 1,2-diisopropyl-1,1,2,2-tetrachlorodisilane

A 500 ml three necked flask was charged with 300 ml of dry benzene and 48.5 g (0.11 mole) of 1,2-diisopropyl-1,1,2,2-tetraphenyldisilane, and the disilane was uniformly dissolved. To the solution was added 1.5 g of anhydrous aluminium chloride While a dry hydrogen chloride gas was introduced into the benzene solution through a needle tube, the flask was heated for a short time to initiate the reaction. After the reaction once began, generation of heat continued for about 20 minutes After the termination of the exothermic reaction, the introduction of the hydrogen chloride gas was stopped. After 2 ml of dry acetone was added in order to inactivate the aluminium chloride, the solvent was distilled away from the reaction mixture. The residue was subjected to a fractional distillation to give 27 g (0.095 mole, 86% yield) of 1,2-diisopropyl-1,1,2,2-tetrachlorodisilane in a colorless clear liquid (b.p. 55° to 57° C./0.45 Torr).

$^1$H NMR (200 MHz, CDCl$_3$)
1.21 (d, 12 H, SiCH(CH$_3$)$_2$)
1.50 (septet, 2 H, SiCH(CH$_3$)$_2$)

Synthesis of 1,2-diethynyl-1,1,2,2-tetramethyldisilane

According to the method described in the literature [1], 1,2-diethynyl-1,1,2,2-tetramethyldisilane was synthesized in a high yield (70 to 80%) by reacting 1,2-dichloro-1,1,2,2-tetramethyldisilane [2] with ethynylmagnesium bromide [3].

(1) Seabald, A.; Seiberlich, P.,; Wrackmeyer, B., J. Organomet. Chem., 303. 73 (1986)

(2) Sakura, H.; Tominaga, K.; Watanabe, T.; Kumada, M, Tetrahedron Lett., 45, 5493 (1966).

(3) Skattebol, L.; Jones, E. R. H.; Whiting, M. C., Org. Synth Coll., 4, 792 (1963)

EXAMPLE 1

Synthesis of bicyclo[6.6.0]-1,8-diisopropyl-4,4,5,5,11,11,12,12-octamethyl-1,4,5,8,11,12-hexasilatetradeca-2,6,9,13-tetrayne tetrayne represented by the following formula (V):

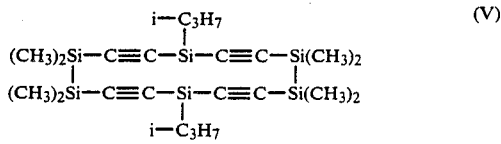

Into a 100 ml flask were placed 1.66 g (10 millimoles) of 1,2-diethynyl-1,1,2,2-tetramethyldisilane and 40 ml of dry THF. To this Was added 10.3 ml (20.6 millimoles) of a 2.0 M solution of ethylmagnesium bromide in THF. A mildly exothermic reaction with generation of ethane was observed. The reaction mixture was refluxed for 2 hours to complete the formation of the diGrignard reagent. The resulting THF solution containing the di-Grignard reagent and a solution prepared by dissolving 1.42g (5 millimoles) of 1,2-diisopropyl-1,1,2,2tetrachlorodisilane in 300 ml of dry THF were simultaneously added dropwise to 100 ml of dry THF in a reaction vessel over 2 hours. After completion of addition, the reaction mixture was refluxed continuously for 3 days to complete the reaction. The reaction mixture was evaporated to distill away the THF. To the residue were added 100 ml of hexane and 100 mil of a saturated aqueous solution of ammonium chloride. The organic layer was washed with a saturated aqueous solution of ammonium chloride (100 ml×2 times) and then with water (100 ml×1 time), and dried over anhydrous sodium sulfate. The drying agent was filtered off and the filtrate was concentrated to give 1.9 g of a crude product in a pale yellow solid. The crude product was recrystallized from ethanol to give 0.51 g (1.1 millimoles, 22% yield) of the desired compound (V) in colorless clear crystals with a melting point of 156° to 157° C.

The following spectral and analytical data for the product support the structure represented by the above formula (V).

IR (KBr disc) cm$^{-1}$: 2960(s), 2920(m), 2890(m), 2870(s), 1470(m), 1410(m), 1250(s), 990(m) None of infrared absorption bands corresponding to Si-H or Si-O-Si were observed.

$^1$H NMR (200 MHz, CDCl$_3$) 0.24 (s, 12 H, Si(CH$_3$)2), 0.27 (s, 12 H, Si(CH$_3$)2), 1.04-1.07 (m, 14 H, SiCH(CH$_3$)2)

$^{13}$C NMR (300 MHz, CDCl$_3$) —3.21 (Si(C$_3$)), —3.02 (Si(C$_3$)2), 13.49 (SiC(CH$_3$)2), 18.49 (SiCH(C$_3$)2), 112.41, 123.34 (acetylenic carbon atom)

$^{29}$Si NMR (300 MHz, CDCl$_3$) —42.87, —33.08

MS (30 eV) m/e: 471 (M$^+$+1, 4), 470 (M$^+$, 11), 428 (23), 427 (19) 113 (100)

The figures in the parentheses mean relative strengthes.

High resolution mass spectroscopic data: Calcd. for C$_{21}$$^{13}$CH$_{38}$Si$_6$: 471.1623, Measured: 471.1608 Calcd for C$_{22}$H$_{38}$Si$_6$: 470.1589, Measured: 470.1618

UV (in n-hexane) λ max (nm): 211, 239, 250 (sh.), 260

EXAMPLE 2

The reactions were carried out in the same manner as in Example 1 except that the reaction of the diGrignard reagent with 1,2-diisopropyl-1,1,2,2-tetrachlorodisilane was carried out in such a manner that the reaction mixture was refluxed for 10 hours and allowed to stand at a room temperature for 14 hours, followed by repetition of such procedures two further times.

After the reaction, the reaction mixture was treated in the same manner as in Example 1 to give a viscous pale yellow liquid containing white particles as a crude product. The crude product was purified by a column chromatography using a silica gel column and a mixed solvent of hexane/ethyl acetate (50/1 by volume) as an eluent, and then by a recrystallization from ethanol, yielding 0.12 g (0.25 millimole, 5% yield) of colorless clear crystals.

The product was confirmed to be identical with that obtained in Example 1 by measurement of the melting point and various spectroscopic analysis.

While the present invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments and equivalents falling within the scope of the appended claims

What we claim is:

1. A condensed bicyclic disilanylene-acetylene compound having the following formula (II):

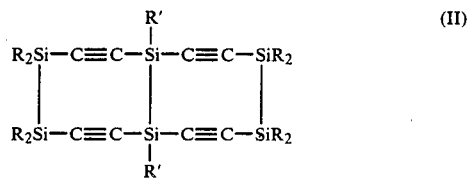

wherein R and R' are each a univalent hydrocarbon group having 1 to 20 carbon atoms.

2. The compound of claim 1, which has a cisconfiguration with respect to the two groups R' bonded to the different silicon atoms in formula (II).

3. The compound of claim 1, which has a transconfiguration with respect to the two groups R' bonded to the different silicon atoms in formula (II).

4. The compound of claim 1, wherein R and R' in formula (II) are selected from the group consisting of CH$_3$, C$_2$H$_5$, n—C$_3$H$_7$, i—C$_3$H$_7$, n—C$_4$H$_9$, i—C$_4$H$_9$, t—C$_4$H$_9$, n—C$_5$H$_{11}$, n—C$_6$H$_{13}$, n—C$_7$H$_{15}$, n—C$_8$H$_{17}$, C$_6$H$_5$ or

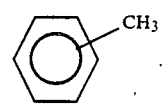

5. The compound of claim 1, wherein R is CH$_3$ and R' is i—C$_3$H$_7$.

6. The compound of claim 1, wherein R is CH$_3$ and R' is C$_6$H$_5$.

7. A method for preparing a condensed bicyclic disilanylene-acetylene compound having the following formula (II);

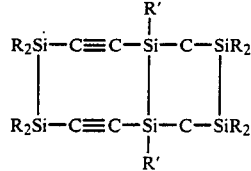 (II)

wherein R and R' are independently a univalent hydrocarbon group having 1 to 20 carbon atoms, comprising the steps of:
(a) forming a diGrignard reagent by reacting a 1,2-diethynyldisilane having the following formula (II):

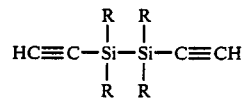 (III)

with a Grignard reagent;
(b) reacting the resulting diGrignard reagent with a 1,1,2,2-tetrachlorodisilane having the following formula (IV):

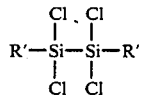 (IV)

and
(c) isolating the resulting condensed bicyclic disilanylene-acetylene compound of formula (II).

8. The method of claim 7, wherein R is selected from the group consisting of $CH_3$, $C_2H_5$, n—$C_3H_7$, i—$C_3H_7$, n—$C_4H_9$ or $C_6H_5$.

9. The method of claim 7, wherein R' is selected from the group consisting of i—$C_3H_7$ or $C_6H_5$.

10. The method of claim 7, wherein R in formula (III) is $CH_3$ and R' in formula (IV) is i—$C_3H_7$.

11. The method of claim 7, wherein R in formula (III) is $CH_3$ and R' in formula (IV) is $C_6H_5$.

12. The method of claim 7, wherein said Grignard reagent is selected from the group consisting of $C_2H_5MgBr$, $CH_3MgBr$, $CH_3MgI$, n—$C_3H_7MgCl$ and $C_6H_5MgCl$.

13. A method for preparing a condensed bicyclic disilanylene-acetylene compound having the following formula (II):

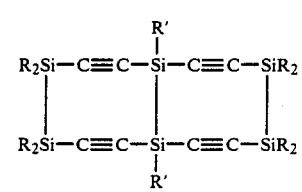 (II)

wherein R and R' are each a univalent hydrocarbon group having 1 to 20 carbon atoms, comprising the steps of:
(a) forming a diGrignard reagent by reacting a 1,2-diethynyldisilane having the following formula (III):

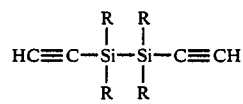 (III)

with a Grignard reagent;
(b) reacting the resulting diGrignard reagent with a 1,1,2,2-tetrachlorodisilane having the following formula (IV);

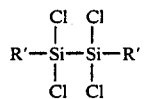 (IV)

and
(c) isolating the resulting condensed bicyclic disilanylene-acetylene compound of formula (II), from the reaction mixture by a solvent extraction.

14. The method of claim 13, wherein R in formula (III) is $CH_3$, $C_2H_5$, n—$C_3H_7$, i—$C_3H_7$, n—$C_4H_9$ or $C_6H_5$.

15. The method of claim 13, wherein R' in formula (IV) is selected from the group consisting of i—$C_3H_7$ or $C_6H_5$.

16. The method of claim 13, wherein R in formula (III) is $CH_3$ and R' in formula (IV) is i—$C_3H_7$.

17. The method of claim 13, wherein R in formula (III) is $CH_3$ and R' in formula (IV) is $C_6H_5$.

18. The method of claim 13, wherein said Grignard reagent is selected from the group consisting of $C_2H_5MgBr$, $CH_3MgBr$, $CH_3MgI$ and $C_6H_5MgCl$.

19. The method of claim 13, wherein each reaction takes place in a tetrahydrofuran solution.

20. The method of claim 19, wherein the reaction of the diGrignard reagent with the 1,1,2,2-tetrachlorodisilane takes place in a dilute tetrahydrofuran solution.

21. The method of claim 13, wherein said solvent for extraction is selected from the group consisting of hexane, pentane, ether, benzene, toluene and chloroform.

* * * * *